(12) United States Patent
Xiao et al.

(10) Patent No.: US 10,191,178 B2
(45) Date of Patent: Jan. 29, 2019

(54) THREE-DIMENSIONAL NUCLEAR MAGNETIC RESONANCE LOGGING INSTRUMENT PROBE, LOGGING INSTRUMENT AND ANTENNA EXCITATION METHOD

(71) Applicant: CHINA UNIVERSITY OF PETROLEUM-BEIJING, Beijing (CN)

(72) Inventors: Lizhi Xiao, Beijing (CN); Xin Li, Beijing (CN); Guangzhi Liao, Beijing (CN); Sihui Luo, Beijing (CN); Zhe Sun, Beijing (CN); Wei Liu, Beijing (CN); Weiliang Chen, Beijing (CN); Jie Wang, Beijing (CN); Kuntie Liao, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 173 days.

(21) Appl. No.: 15/258,787

(22) Filed: Sep. 7, 2016

(65) Prior Publication Data
US 2017/0082774 A1 Mar. 23, 2017

(30) Foreign Application Priority Data
Sep. 23, 2015 (CN) .......................... 2015 1 0613872

(51) Int. Cl.
*G01V 3/32* (2006.01)
*G01R 33/34* (2006.01)
(Continued)

(52) U.S. Cl.
CPC .......... *G01V 3/32* (2013.01); *G01R 33/34092* (2013.01)

(58) Field of Classification Search
CPC .................. G01V 3/32; G01R 33/3808; G01R 33/34092; G01R 33/341; G01R 33/3415;
(Continued)

(56) References Cited

U.S. PATENT DOCUMENTS 6,522,137 B1 * 2/2003 Sun ...................... G01N 24/081
324/303
6,586,932 B1 7/2003 Taherian et al. .............. 324/303

FOREIGN PATENT DOCUMENTS

CN 1248705 A 3/2000
CN 102013299 A 4/2011
(Continued)

OTHER PUBLICATIONS

The Chinese First Examination Report of corresponding Chinese patent application No. 201510613872.X, dated Jun. 20, 2017.

*Primary Examiner* — Rishi R Patel
(74) *Attorney, Agent, or Firm* — J.C. Patents

(57) ABSTRACT

The present invention provides a three-dimensional nuclear magnetic resonance logging instrument probe, a logging instrument and an antenna excitation method, where the probe includes: a probe framework, a magnet and an antenna; four magnets are uniformly distributed along a circumference of the probe framework, the magnets are magnetized in a radial direction of the probe framework, two magnets placed opposite to each other are magnetized from outside to inside, and the other two magnets placed opposite to each other are magnetized from inside to outside; in the probe framework, each of the magnets is provided with independently fed antennas; antennas corresponding to each of the magnets comprise a left antenna provided on one side of the corresponding magnet and a right antenna provided on the other side of the corresponding magnet; the left antenna and the right antenna corresponding to each magnet are electrically connected.

9 Claims, 6 Drawing Sheets

(51) Int. Cl.
*E21B 49/00* (2006.01)
*G01V 3/14* (2006.01)

(58) Field of Classification Search
CPC ... G01R 33/383; G01R 33/445; G01N 24/081
See application file for complete search history.

(56) References Cited

FOREIGN PATENT DOCUMENTS

| | | |
|---|---|---|
| CN | 102331588 A | 1/2012 |
| CN | 102650208 A | 8/2012 |
| CN | 202510100 U | 10/2012 |
| CN | 203383806 U | 1/2014 |
| CN | 203594440 U | 5/2014 |

\* cited by examiner

THREE-DIMENSIONAL NUCLEAR MAGNETIC RESONANCE LOGGING INSTRUMENT PROBE, LOGGING INSTRUMENT AND ANTENNA EXCITATION METHOD

CROSS-REFERENCE TO RELATED APPLICATIONS

This application claims priority to Chinese Patent Application No. 201510613872.X, filed on Sep. 23, 2015, the content of which is hereby incorporated by reference in its entirety.

TECHNICAL FIELD

The present invention relates to the technical field of nuclear magnetic resonance logging, and more particularly to a three-dimensional nuclear magnetic resonance logging instrument probe, a logging instrument and an antenna excitation method.

BACKGROUND

The phenomenon of nuclear magnetic resonance (Nuclear Magnetic Resonance, NMR) is, shortly after its discovery in 1946, applied in fields, such as physics, chemistry, material science, life science and medical science. In 1950s, the nuclear magnetic resonance came into use in the fossil oil and natural gas industry, and originally applied to the field of oil reservoir rock physics. A nuclear magnetic resonance logging instrument can utilize the nuclear magnetic resonance principle to detect stratum information around the borehole, and have unique capabilities of qualitative recognition and quantitative evaluation for the reservoir fluid.

A probe is one of the important parts in the nuclear magnetic resonance logging instrument, and the structure of the probe determines key performances, such as a measuring mode of the instrument, a nuclear magnetic resonance region and nuclear magnetic resonance signal intensity. The nuclear magnetic resonance logging instrument probe mainly includes a magnet and an antenna, the magnet can form a static magnetic field for polarizing a spin hydrogen proton, and the antenna can emit a radio frequency field for reversing the spin hydrogen proton, and after the radio frequency field is removed, the spin hydrogen proton starts to precess along the static magnetic field, and thereby generates an nuclear magnetic resonance inductive signal, and the stratum situation can be analyzed by detecting the nuclear magnetic resonance inductive signal.

The existing nuclear magnetic resonance logging instrument probe usually adopts a column-shaped magnet, both rounded sides of the magnet are an N pole and a S pole, respectively, the magnetic field distribution is formed by closed magnetic lines of force pointing from the N pole to the S pole, the antenna surrounds the magnet, and can excite polarized stratum region all around the borehole by 360°, so that there is no detection blind zone around the borehole, and multi-frequency multi-slice measurement can be performed, but the signal obtained by measurement is only an average signal of signals in the 360-degree stratum. Accordingly, the nuclear magnetic resonance logging instrument probe in the prior art only can perform signal detection in radial depth dimension and axial depth dimension, but has no capability to detect signals in the circumferential multi-azimuth sensitive area.

SUMMARY

The present invention provides a three-dimensional nuclear magnetic resonance logging instrument probe, a logging instrument and an antenna excitation method, so as to solve the technical problems that the nuclear magnetic resonance logging instrument probe in the prior art only can perform signal detection in radial depth dimension and axial depth dimension, but have no capability to detect signals in the circumferential multi-azimuth sensitive area.

The present invention provides a three-dimensional nuclear magnetic resonance logging instrument probe, including: a probe framework, a magnet and an antenna;

The number of the magnet is four, and they are uniformly distributed along the circumference of the probe framework, the magnets are magnetized in a radial direction of the probe framework, wherein two magnets placed opposite to each other are magnetized from outside to inside, and the other two magnets placed opposite to each other are magnetized from inside to outside;

In the probe framework, each of the magnets is provided with independently fed antennas;

Antennas corresponding to each of the magnets comprise a left antenna provided on one side of the corresponding magnet and a right antenna provided on the other side of the corresponding magnet;

The left antenna and the right antenna that correspond to each magnet are electrically connected.

Furthermore, in two adjacent magnets, the front magnet and the rear magnet are respectively magnetized in two directions perpendicular to each other;

The antenna, in the two antennas corresponding to the front magnet, closest to the rear magnet and the antenna, in the two antennas corresponding to the rear magnet, closest to the front magnet, are connected via a switch.

Furthermore, the antenna is a strip-type antenna made from deoxidized copper sheet;

In two antennas for each magnet, the distance from the left antenna to the magnet is equal to the distance from the right antenna to the magnet;

In the eight antennas corresponding to the four magnets, the distance between the left antenna and the right antenna for each magnet is equal to a preset distance value.

Furthermore, the probe framework is provided with four receiving chambers matched with the magnets, and the magnets are fixed within the receiving chambers;

The probe framework is arranged with eight grooves, the antennas are arranged in the grooves and the grooves are filled with high magnetic permeable materials.

Furthermore, the three-dimensional nuclear magnetic resonance logging instrument probe further includes: an antenna excitation device for feeding the antenna;

In the two antennas corresponding to each magnet, one end of the left antenna and one end of the right antenna are connected, the other end of the left antenna and the other end of the right antenna are connected to the antenna excitation device.

Furthermore, the probe framework is provided with a through hole, the central axis of the through hole coincides with the central axis of the probe framework;

A support frame penetrates through the through hole, and is fixedly connected to the housing of the probe, or alternatively, a diversion pipe for drilling fluid flowing through is arranged in the through hole, and the diversion pipe is fixedly connected to the probe framework via a metal piece.

Furthermore, each magnet includes a plurality of magnetic sheets;

The plurality of magnetic sheets are fixed via an adhesive, to form the magnet.

Furthermore, the magnet is a samarium cobalt permanent magnet.

The present invention also provides a logging instrument, including any one of the three-dimensional nuclear magnetic resonance logging instrument probes described above.

The present invention also provides an antenna excitation method based on any one of the three-dimensional nuclear magnetic resonance logging instrument probes described above, comprising:

Exciting two antennas corresponding to one magnet, to generate a sensitive area range of 45° angle and achieve a downhole detection at a mono-azimuth 45° angle;

Exciting four antennas corresponding to two adjacent magnets, to generate a sensitive area range of 90° angle and achieve a downhole detection at a mono-azimuth 90° angle;

Exciting all antennas, to generate a sensitive area range of 360° angle and achieve a downhole omni-directional detection.

In the three-dimensional nuclear magnetic resonance logging instrument probe, the logging instrument and the antenna excitation method provided in the present invention, four magnets are uniformly distributed along the circumference of the probe framework, both sides of each of the magnets are provided correspondingly with two independently fed antennas, and stratum information detection at different azimuth angles can be achieved by exciting different antennas, so that circumferential recognizing capability of the nuclear magnetic resonance logging instrument probe can be improved and three-dimensional, i.e., radial, axial and circumferential, stratum detection can be achieved.

DESCRIPTION OF REFERENCE SIGNS

10—Probe framework 11—Eastern magnet 12—Southern magnet 13—Western magnet 14—Northern magnet 21—Left antenna of an eastern magnet 22—Right antenna of an eastern magnet 23—Left antenna of a southern magnet 24—Right antenna of a southern magnet 25—Left antenna of a western magnet 26—Right antenna of a western magnet 27—Left antenna of a northern magnet 28—Right antenna of a northern magnet 31—Lifting direction 32—Lowering direction 4—Sensitive area slice 5—Magnetic sheet 6—Groove 7—Through hole 9—Vertical well

Description of Embodiments

In order to make the objects, technical solutions, and advantages of the embodiments of the present invention clearer, the technical solutions in the embodiments of the present invention are hereinafter described clearly and completely with reference to the accompanying drawings of the embodiments of the present invention. Obviously, the embodiments described here are part of the embodiments of the present invention and not all of the embodiments. All other embodiments obtained by persons skilled in the art without any creative efforts, on the basis of the embodiments of the present invention, will all fall within the scope of the invention.

Embodiment 1

Figure 1:
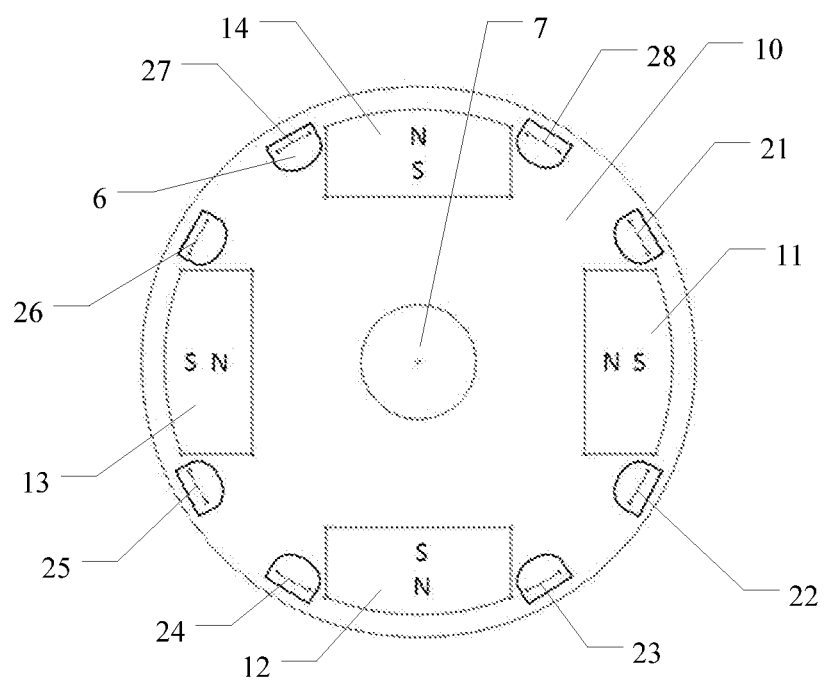
FIG. 1 is a structural schematic diagram of a three-dimensional nuclear magnetic resonance logging instrument probe according to Embodiment 1 of the present invention.

Embodiment 1 of the present invention provides a three-dimensional nuclear magnetic resonance logging instrument probe. FIG. 1 is a structural schematic diagram of a three-dimensional nuclear magnetic resonance logging instrument probe according to Embodiment 1 of the present invention. As shown in FIG. 1, the three-dimensional nuclear magnetic resonance logging instrument probe in this embodiment may include a probe framework 10, a magnet and an antenna;

The number of the magnet is four, and they are uniformly distributed along a circumference of the probe framework 10, the magnets are magnetized in a radial direction of the probe framework 10, wherein two magnets placed opposite to each other are magnetized from outside to inside, and the other two magnets placed opposite to each other are magnetized from inside to outside;

In the probe framework 10, each of the magnets is provided with independently fed antennas;

Antennas corresponding to the magnets comprise a left antenna provided on one side of the magnets and a right antenna provided on the other side of the magnets;

The left antenna and the right antenna corresponding to each of the magnets are electrically connected.

Specifically, the probe framework 10 can be made from non-high magnetic permeable materials with high mechanical hardness, such as titanium alloy, so as to guarantee pressure resistance and anti-torsion capabilities of the whole probe. The probe framework 10 can have a cylindrical structure, and four magnets are uniformly distributed along a circumference of the probe framework, that is to say, distances between each of four magnets and a central axis of the probe framework 10 are all the same, and distances between any two magnets are also the same.

The probe framework 10 can be provided with four receiving chambers matched with the magnets, and the magnets are fixed within the receiving chambers, shapes and sizes of the receiving chambers and the magnets are consistent, so as to keep relative positions of the magnets unchanged when the probe measures in a movable manner, and guarantee stability of the static magnetic field.

The four magnets in this embodiment can be distributed in four directions of east, south, west, and north with reference to the center of the probe framework 10 according to the compass bearing, for illustrative purposes, the four magnets are referred to as an eastern magnet 11, a southern magnet 12, a western magnet 13 and a northern magnet 14, respectively. The southern magnet 12 and the northern magnet 14 are placed opposite to each other, the eastern magnet 11 and the western magnet 13 are placed opposite to each other.

The magnet is magnetized in a radial direction of the probe framework 10, that is, the magnet is magnetized from inside to outside or from outside to inside. Particularly, two magnets placed opposite to each other are magnetized from outside to inside, and the other two magnets placed opposite to each other are magnetized from inside to outside, in this embodiment, the southern magnet 12 and the northern magnet 14 are magnetized from inside to outside, the eastern magnet 11 and the western magnet 13 are magnetized from outside to inside. The magnetism of the four magnets after magnetized is shown in FIG. 1, where letters S and N indicate an S pole and an N pole of each magnet, respectively.

For each magnet, the generated magnetic lines of force all start from the N pole, and return to the S pole, in this embodiment, since the N poles and the S pole of the eastern magnet 11 and the western magnet 13 are inside and outside, respectively, and the N poles and the S pole of the southern magnet 12 and the northern magnet 14 are outside and inside, respectively, then the generated magnetic lines of force will start from the N pole of one magnet, and enter the S pole of another magnet.

Figure 2:
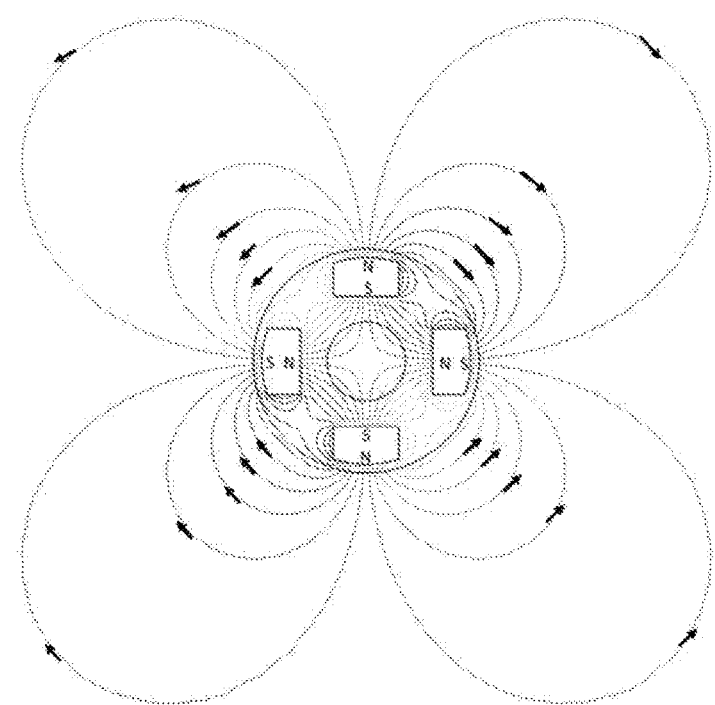
FIG. 2 is a schematic diagram illustrating the distribution of magnetic lines of force of a static magnetic field generated by a magnet of the three-dimensional nuclear magnetic resonance logging instrument probe according to Embodiment 1 of the present invention.

FIG. 2 is a schematic diagram illustrating the distribution of magnetic lines of force of a static magnetic field generated by a magnet of the three-dimensional nuclear magnetic resonance logging instrument probe according to Embodiment 1 of the present invention. As shown in FIG. 2, the magnetic lines of force start from the N pole of one magnet, and return to the S pole of a magnet adjacent to the magnet after passing the stratum. The static magnetic fields generated by the four magnets all have the same magnetic field intensities at different azimuth angles in the same radial depth.

In the probe framework 10, each magnet is provided at each side with antennas correspondingly, in particular, the probe framework 10 is arranged with eight grooves 6, the antennas are arranged in the grooves 6, and the grooves 6 can be filled with high magnetic permeable materials, which can improve the antenna efficiency and guarantee a depth of the sensitive area. The antenna can be a strip-type antenna made from deoxidized copper sheet, or of other types, and this embodiment is not limited thereto.

As viewed from the central position of the probe, the antenna on the left of the magnet is called a left antenna, and the antenna on the right of the magnet is called a right antenna. The eight antennas in the probe framework 10 are fed independently, excitation signals are transmitted to one of the antennas, which will not affect other antennas.

In the two antennas corresponding to each magnet, a distance from the left antenna to the magnet is equal to the distance from the right antenna to the magnet; in the eight antennas corresponding to the four magnets, distances between the left antenna and the right antenna corresponding to each magnet are all equal to a preset distance value.

Figure 3:
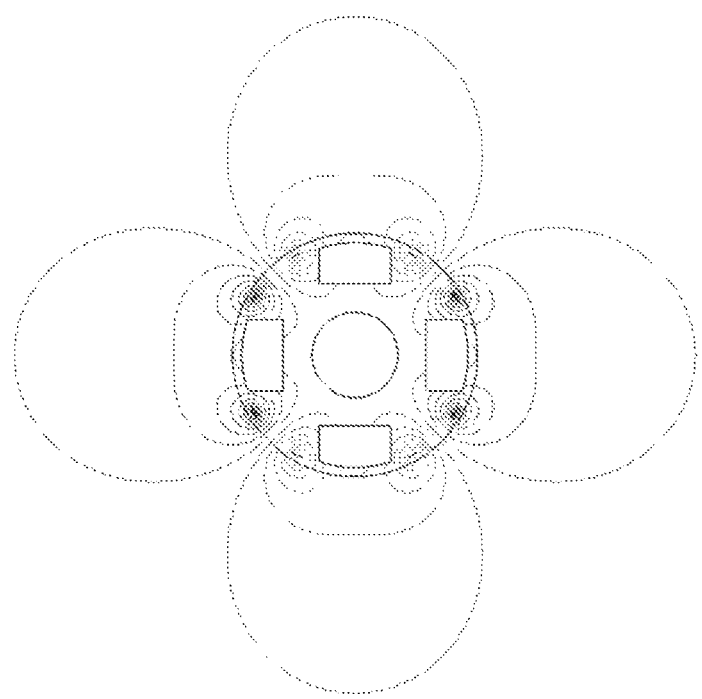
FIG. 3 is a schematic diagram illustrating the distribution of magnetic lines of force of a radio frequency field generated by an antenna of the three-dimensional nuclear magnetic resonance logging instrument probe according to Embodiment 1 of the present invention.

FIG. 3 is a schematic diagram illustrating the distribution of magnetic lines of force of a radio frequency field generated by an antenna of the three-dimensional nuclear magnetic resonance logging instrument probe according to Embodiment 1 of the present invention. FIG. 3 illustrates the distribution of magnetic lines of force of radio frequency fields generated when eight antennas are all excited, as shown in FIG. 3, the radio frequency fields generated by the eight antennas are centro-symmetric.

The left antenna and the right antenna corresponding to each magnet are electrically connected, in operation, the left antenna and the right antenna of one magnet can be excited simultaneously, so as to generate a sensitive area range of 45° and achieve a downhole detection at an mono-directional 45° angle; four antennas corresponding to two adjacent magnets also can be excited, so as to generate a sensitive area range of 90° and achieve a downhole detection at a mono-azimuth 90° angle; all the antennas also can be excited, so as to generate a sensitive area range of 360° and achieve a downhole omni-directional detection. Table 1 shows 13 types of different antenna excitation modes in this embodiment.

TABLE 1

| Mode | Excited antenna | Sensitive area |
| --- | --- | --- |
| 1 | 21, 22 | 45° in the East |
| 2 | 23, 24 | 45° in the South |
| 3 | 25, 26 | 45° in the West |
| 4 | 27, 28 | 45° in the North |
| 5 | 21, 22, 23, 24 | 90° in the Southeast |
| 6 | 23, 24, 25, 26 | 90° in the Southwest |
| 7 | 25, 26, 27, 28 | 90° in the Northwest |
| 8 | 27, 28, 21, 22 | 90° in the Northeast |
| 9 | 21, 22, 23, 24, 25, 26, 27, 28 | Omni-direction |

In Table 1, antenna 21 and antenna 22 are the left antenna and the right antenna corresponding to the eastern magnet 11, respectively, antenna 23 and antenna 24 are the left antenna and the right antenna corresponding to the southern magnet 12, respectively, antenna 25 and antenna 26 are the left antenna and the right antenna corresponding to the western magnet 13, respectively, antenna 27 and antenna 28 are the left antenna and the right antenna corresponding to the northern magnet 14, respectively. As can be seen from Table 1, stratum information at different azimuth angles can be detected by exciting different antennas, so that the nuclear magnetic resonance logging instrument probe can have a circumferential recognizing capability.

One of the basic conditions for the nuclear magnetic resonance is that, the transmitting frequency of the antenna should be equal to the Larmor frequency of the polarized hydrogen protons in the stratum, and the Larmor frequency can be expressed by the following formula:

$$f_0 = \frac{\gamma}{2\pi} B_0, \tag{1}$$

where, $f_0$ is the Larmor frequency, $B_0$ is a static magnetic field intensity, and $\gamma$ is the gyromagnetic ratio, $$\frac{\gamma}{2\pi} = 42.58 \text{ MHz}/T.$$

The static magnetic field intensities are different at different radial depths, that is, hydrogen protons at different radial depths have different Larmor frequencies, radio frequency pulses with a certain bandwidth corresponding to the Larmor frequency are transmitted to the antenna, so that a plurality of sensitive area slices at different depths can be formed radially, and the probe can detect signals at a radial dimension; according to the arrangement manner of the magnets and the antennas in this embodiment, sensitive area slices at a plurality of azimuths can be formed around the probe, and each slice is in the shape of a tile shell having a certain arc. A number of sensitive area slices can be formed by combing radial and circumferential directions, for example, if the antenna has 5 operating frequencies, then 9×5=45 sensitive area slices can be formed.

During the downhole detection, stratum information at different axial depths can be detected by lifting or lowering the probe; stratum information at different radial depths can be detected by changing an excitation frequency of the antenna; and stratum information at different azimuth angles can be detected by exciting different antennas. Therefore, a three-dimensional detection capability of the probe can be achieved by combining signals at an axial depth dimension, a radial depth dimension and a circumferential azimuth angle. In this embodiment, the axial direction refers to an extending direction of the central axis of the well, the radial direction refers to an extending direction of the well center along the radius, and the circumferential direction refers to an extending direction around the well center.

In the three-dimensional nuclear magnetic resonance logging instrument probe provided in this embodiment, four magnets are uniformly distributed along a circumference of the probe framework 10, both sides of each magnet are provided correspondingly with two independently fed antennas, stratum information detection at different azimuth angles can be achieved by exciting different antennas, so that circumferential recognizing capability of the nuclear magnetic resonance logging instrument probe can be improved and three-dimensional (radial, axial and circumferential) stratum detection can be achieved.

Embodiment 2

Embodiment 2 of the present invention provides a three-dimensional nuclear magnetic resonance logging instrument probe. The three-dimensional nuclear magnetic resonance logging instrument probe in this embodiment is on the basis of the three-dimensional nuclear magnetic resonance logging instrument probe provided in Embodiment 1, the improvements are as follows:

In the two adjacent magnets, a front magnet and a rear magnet are respectively magnetized in two directions perpendicular to each other; the antenna in the two antennas corresponding to the front magnet closest to the rear magnet and the antenna in the two antennas corresponding to the rear magnet closest to the front magnet are connected via a switch.

Specifically, the adjacent two magnets refer to two magnets which are respectively magnetized in two directions perpendicular to each other, one is as the front magnet, and the other is as the rear magnet. For example, for the adjacent eastern magnet 11 and southern magnet 12, the eastern magnet 11 is as the front magnet, and the southern magnet 12 is as the rear magnet, of course, vice versa. The eastern magnet 11 corresponds to the antennas 21 and 22, the one in the antennas 21 and 22 closer to the southern magnet 12 is the antenna 22, the southern magnet 12 corresponds to the antennas 23 and 24, the one in the antennas 23 and 24 closer to the eastern magnet 11 is the antenna 23, and therefore, the antennas 22 and 23 are connected via a switch.

In this embodiment, besides exciting antenna 21 and antenna 22 to generate a sensitive area range of 45°, also can turn the switch between the antennas 22 and 23 on to excite antenna 22 and antenna 23 to generate a sensitive area range of 45°. When there is no need to detect the sensitive area corresponding to the antennas 22 and 23, the switch between the antennas 22 and 23 can be turned off.

Similarly, the antennas 24 and 25 are connected via a switch, the antennas 26 and 27 are connected via a switch, and the antennas 28 and 21 are connected via a switch. Table 2 shows 4 types of antenna excitation modes when each switch is turned on. When there is no need to detect the four areas given in Table 2, corresponding switches can be turned off, and antennas are excited according to the 9 types of excitation modes given in Table 1 in Embodiment 1.

TABLE 2

| Mode | Excited antenna | Sensitive area |
| --- | --- | --- |
| 10 | 22, 23 | 45° in the Southeast |
| 11 | 24, 25 | 45° in the Southwest |
| 12 | 26, 27 | 45° in the Northwest |
| 13 | 28, 21 | 45° in the Northeast |

In this embodiment, there are a plurality of detecting modes by combining Table 1 and Table 2. When four-sector detection is needed, antennas are excited according to modes 5, 6, 7, 8; when eight-sector detection is needed, antennas are excited according to modes 1, 2, 3, 4, 10, 11, 12, 13; when omni-directional stratum information detection is needed, antennas are excited according to mode 9.

Figure 4:
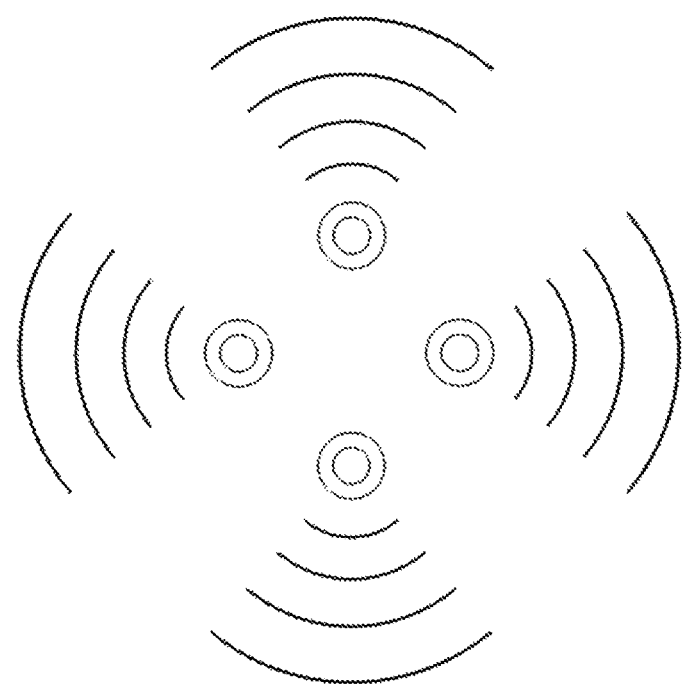
FIG. 4 is a schematic diagram of four types of 90° sensitive area slices formed by a three-dimensional nuclear magnetic resonance logging instrument probe according to Embodiment 2 of the present invention.
Figure 5:
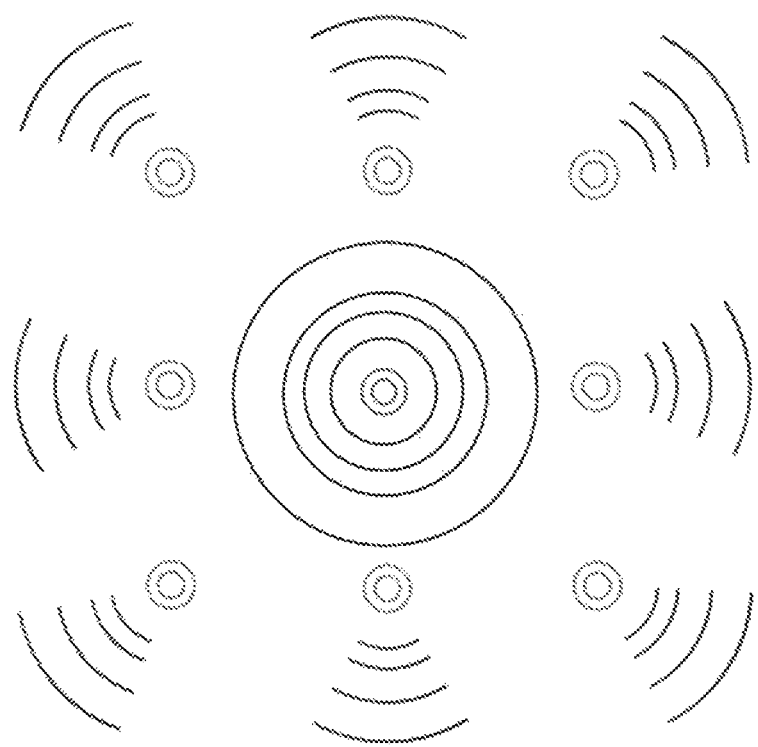
FIG. 5 is a schematic diagram of eight types of 45° sensitive area slices and 360° sensitive area slices formed by a three-dimensional nuclear magnetic resonance logging instrument probe according to Embodiment 2 of the present invention.

FIG. 4 is a schematic diagram of four types of 90° sensitive area slices formed by a three-dimensional nuclear magnetic resonance logging instrument probe according to Embodiment 2 of the present invention. FIG. 5 is a schematic diagram of eight types of 45° sensitive area slices and 360° sensitive area slices formed by a three-dimensional nuclear magnetic resonance logging instrument probe according to Embodiment 2 of the present invention.

In FIG. 4 and FIG. 5, the circle in the figures indicates a three-dimensional nuclear magnetic resonance logging instrument probe, the arc near the circle indicates a sensitive area slice. As shown in FIG. 4, the left portion illustrates a positional relationship between the probe and the sensitive area slice when the sensitive area is 90° in the west, the right portion illustrates a positional relationship between the probe and the sensitive area slice when the sensitive area is 90° in the east, the upper portion illustrates a positional relationship between the probe and the sensitive area slice when the sensitive area is 90° in the north, and the lower portion illustrates a positional relationship between the probe and the sensitive area slice when the sensitive area is 90° in the south. As shown in FIG. 5, the first row illustrates a positional relationship between the probe and the sensitive area slice when the sensitive areas are 45° in the northwest, 45° in the north, and 45° in the northeast, respectively, the third row illustrates a positional relationship between the probe and the sensitive area slice when the sensitive areas are 45° in the southwest, 45° in the south, and 45° in the southeast, respectively, the middle portion of the second row illustrates a positional relationship between the probe and the sensitive area slice when the sensitive areas are omni-directional, left and right portions of the second row illustrate a positional relationship between the probe and the sensitive area slice when the sensitive areas are 45° in the west and 45° in the east, respectively.

Figure 6:
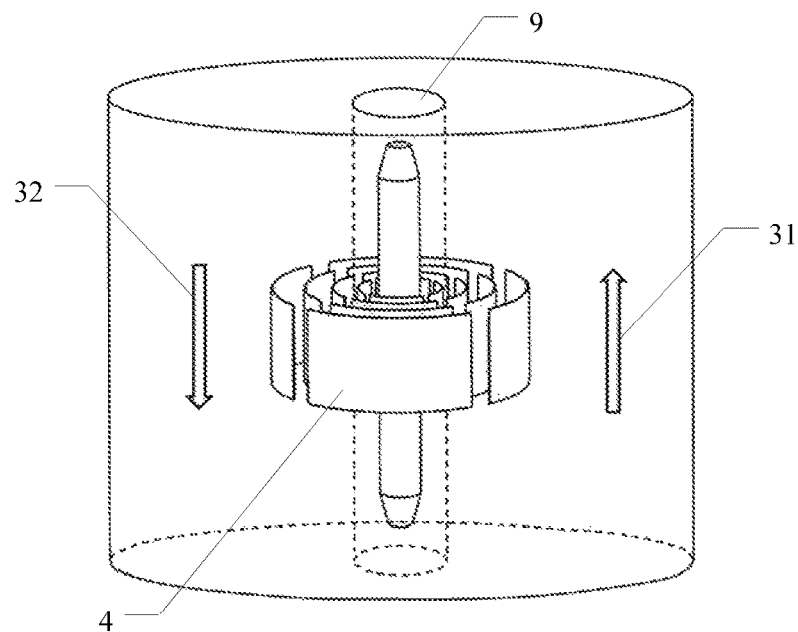
FIG. 6 is a schematic diagram of three-dimensional detection of a three-dimensional nuclear magnetic resonance logging instrument probe according to Embodiment 2 of the present invention.

FIG. 6 is a schematic diagram of three-dimensional detection of a three-dimensional nuclear magnetic resonance logging instrument probe according to Embodiment 2 of the present invention. As shown in FIG. 6, when detection is performed in a vertical well 9, the probe moves in a lifting direction 31 or a lowering direction 32, and stratum information detection at an axial depth dimension can be achieved; stratum information detection at a radial depth dimension can be achieved by changing an excitation frequency of the antenna; and stratum information detection at a circumferential azimuth angle can be achieved by exciting different antennas.

In the adjacent two magnets of the three-dimensional nuclear magnetic resonance logging instrument probe in this embodiment, the antenna in the two antennas corresponding to the front magnet closest to the rear magnet and the antenna in the two antennas corresponding to the rear magnet closest to the front magnet are connected via a switch, so that more antenna excitation modes can be provided, more sensitive areas are added, and circumferential detecting capability of the probe can be further improved.

Besides, the number of the magnets and antennas can be further increased on the basis of the technical solutions in the above embodiments, for example, the number of magnets can be increased to 8 or 16, the number of antennas can be increased to 16 or 32, so that more sensitive area slices 4 can be generated in the circumferential direction of the probe, and the circumferential recognizing capability of the probe can be improved.

On the basis of the technical solutions in the above embodiments, it is preferable that the nuclear magnetic resonance logging instrument probe also includes: an antenna excitation device for feeding the antenna; in the two antennas corresponding to each magnet, one end of the left antenna and one end of the right antenna are connected, the other end of the left antenna and the other end of the right antenna are connected to the antenna excitation device, respectively.

The antenna excitation device can include a plurality of excitation channels, each excitation channel is electrically connected to an antenna, so that excitation signals can be provided to the antenna, and a sensitive area slice 4 at different azimuth angles can be generated by providing excitation signals to different antennas.

Besides, the antenna excitation device can be connected to a control end of the switch, so that the switch can be controlled to be turned on or off, and multiple antenna excitation modes can be achieved.

On the basis of the technical solutions in the above embodiments, it is preferable that the probe framework 10 is provided with a through hole 7, a central axis of the through hole 7 coincides with the central axis of the probe framework 10.

In terms of a cable-type nuclear magnetic resonance logging instrument, a support frame can penetrate through a through hole 7, and be fixedly connected to the housing of the probe, for providing a mechanical support for the probe; in terms of a nuclear magnetic resonance logging-while-drilling instrument, a diversion pipe for drilling fluid flowing through is arranged in the through hole 7, and the diversion pipe is fixedly connected to the probe framework 10 via a metal piece.

On the basis of the technical solutions in the above embodiments, it is preferable that the magnet can be a samarium cobalt permanent magnet. The samarium cobalt permanent magnet has a better temperature coefficient and a larger coercive force. The shape of the magnet can be irregular, so that the magnet can be manufactured easily and magnetized conveniently, and does not occupy too much space.

Figure 7:
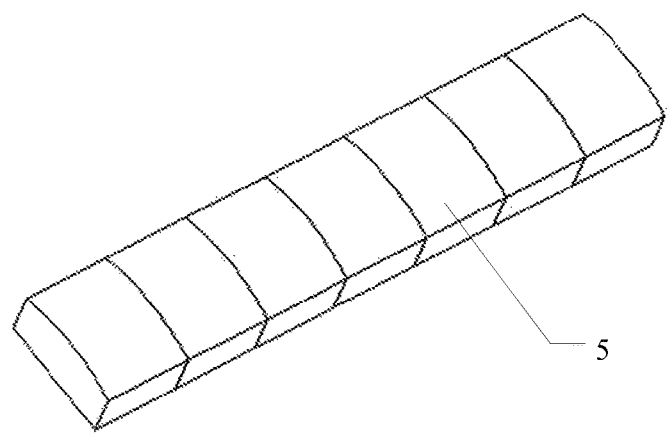
FIG. 7 is a structural schematic diagram of a magnet in a three-dimensional nuclear magnetic resonance logging instrument probe according to Embodiment 2 of the present invention.

Furthermore, each magnet can include a plurality of magnetic sheets. FIG. 7 is a structural schematic diagram of a magnet in a nuclear magnetic resonance logging instrument probe according to Embodiment 2 of the present invention. As shown in FIG. 7, the plurality of magnetic sheets 5 have the same shapes, sizes and properties, the plurality of magnetic sheets 5 are fixed via an adhesive to form the magnet.

Embodiment 3

Embodiment 3 of the present invention provides a logging instrument including the three-dimensional nuclear magnetic resonance logging instrument probe according to any of the above embodiments. Structures and functions for various portions of the three-dimensional nuclear magnetic resonance logging instrument probe in this embodiment are similar to those in the above embodiments, and therefore no more details are given herein.

In the logging instrument provided in this embodiment, four magnets are uniformly distributed along a circumference of the probe framework 10, both sides of each magnet are provided correspondingly with two independently fed antennas, stratum information detection at different azimuth angles can be achieved by exciting different antennas, so that circumferential recognizing capability of the nuclear magnetic resonance logging instrument probe can be improved and three-dimensional, i.e., radial, axial and circumferential, stratum detection can be achieved.

Embodiment 4

Embodiment 4 of the present invention provides an antenna excitation method based on the three-dimensional nuclear magnetic resonance logging instrument probe according to any of the above embodiments, which includes:

Exciting two antennas corresponding to one magnet, to generate a sensitive area range of 45° angle and achieve a downhole detection at a mono-azimuth 45° angle;

Exciting four antennas corresponding to two adjacent magnet, to generate a sensitive area range of 90° angle and achieve a downhole detection at a mono-azimuth 90° angle;

Exciting all antennas, to generate a sensitive area range of 360° angle and achieve a downhole omni-directional detection.

Principles for implementing various steps in this embodiment are similar to those in the above embodiments, and therefore no more details are given herein.

In the antenna excitation method provided in this embodiment, stratum information detection at different azimuth angles can be achieved by exciting different antennas, so that circumferential recognizing capability of the nuclear magnetic resonance logging instrument probe can be improved and three-dimensional, i.e., radial, axial and circumferential, stratum detection can be achieved.

Finally, it should be noted that the above embodiments are merely provided for describing the technical solutions of the present invention, but not intended to limit the present invention. It should be understood by persons skilled in the art that although the present invention has been described in detail with reference to the foregoing embodiments, modifications can be made to the technical solutions described in the foregoing embodiments, or equivalent replacements can be made to partial or all technical features in the technical solutions; however, such modifications or replacements do not cause the essence of corresponding technical solutions to depart from the scope of the embodiments of the present invention.

What is claimed is:

1. A three-dimensional nuclear magnetic resonance logging instrument probe, comprising: a probe framework, four magnets and eight independently fed antennas; wherein the four magnets are uniformly distributed along a circumference of the probe framework, the magnets are magnetized in a radial direction of the probe framework, wherein, two magnets placed opposite to each other are magnetized from outside to inside, and the other two magnets placed opposite to each other are magnetized from inside to outside;

in the probe framework, each of the magnets is provided with two antennas;

the two antennas corresponding to each of the magnets comprise a left antenna provided on one side of the corresponding magnet and a right antenna provided on the other side of the corresponding magnet;

the left antenna and the right antenna corresponding to each of the four magnets are electrically connected;

the probe framework is provided with four receiving chambers matched with the four magnets, and the four magnets are fixed within the four receiving chambers;

the probe framework is arranged with eight grooves, the eight antennas are arranged in the eight grooves and the eight grooves are filled with high magnetic permeable materials.

2. The three-dimensional nuclear magnetic resonance logging instrument probe according to claim 1, wherein:

in two adjacent magnets, a front magnet and a rear magnet are respectively magnetized in two directions perpendicular to each other;

an antenna that is one of two antennas corresponding to the front magnet and is closest to the rear magnet and an antenna that is one of two antennas corresponding to the rear magnet and is closest to the front magnet are connected via a switch.

3. The three-dimensional nuclear magnetic resonance logging instrument probe according to claim 1, wherein, each of the antennas is a strip-type antenna made from deoxidized copper sheet;

in the two antennas corresponding to each of the magnets, a distance from the left antenna to the corresponding magnet is equal to the distance from the right antenna to the corresponding magnet;

in the eight antennas corresponding to the four magnets, a distance between the left antenna and the right antenna corresponding to each of the magnets is equal to a preset distance value.

4. The three-dimensional nuclear magnetic resonance logging instrument probe according to claim 1, further comprising: an antenna excitation device for feeding each of the antennas;

in the two antennas corresponding to each of the magnets, one end of the left antenna and one end of the right antenna are connected, the other end of the left antenna and the other end of the right antenna are connected to the antenna excitation device.

5. The three-dimensional nuclear magnetic resonance logging instrument probe according to claim 1, wherein the probe framework is provided with a through hole, a central axis of the through hole coincides with a central axis of the probe framework;

a support frame penetrates through the through hole, and is fixedly connected to a housing of the probe, or a diversion pipe for drilling fluid flowing through is arranged in the through hole, and the diversion pipe is fixedly connected to the probe framework via a metal piece.

6. The three-dimensional nuclear magnetic resonance logging instrument probe according to claim 5, wherein each of the magnets comprises a plurality of magnetic sheets;

the plurality of magnetic sheets are fixed via an adhesive to form the magnet.

7. The three-dimensional nuclear magnetic resonance logging instrument probe according to claim 5, wherein each of the magnets is a samarium cobalt permanent magnet.

8. A logging instrument comprising the three-dimensional nuclear magnetic resonance logging instrument probe according to claim 1.

9. An antenna excitation method based on the three-dimensional nuclear magnetic resonance logging instrument probe according to claim 1, comprising:

exciting the two antennas corresponding to each of the magnets, to generate a sensitive area range of 45° angle and achieve a downhole detection at a mono-azimuth 45° angle;

exciting four antennas corresponding to two adjacent magnets, to generate a sensitive area range of 90° angle and achieve a downhole detection at a mono-azimuth 90° angle;

exciting all antennas, to generate a sensitive area range of 360° angle and achieve a downhole omni-directional detection.

* * * * *